United States Patent
Noruzinia et al.

(10) Patent No.: US 12,090,177 B2
(45) Date of Patent: Sep. 17, 2024

(54) CONDITIONED STEM CELL-DERIVED EXTRACT

(71) Applicants: Mehrdad Noruzinia, Tehran (IR); Oranous Bashti Shiraz, Tehran (IR)

(72) Inventors: Mehrdad Noruzinia, Tehran (IR); Oranous Bashti Shiraz, Tehran (IR)

(*) Notice: Subject to any disclaimer, the term of this patent is extended or adjusted under 35 U.S.C. 154(b) by 778 days.

(21) Appl. No.: 16/251,124

(22) Filed: Jan. 18, 2019

(65) Prior Publication Data

US 2019/0151374 A1    May 23, 2019

Related U.S. Application Data

(60) Provisional application No. 62/619,168, filed on Jan. 19, 2018.

(51) Int. Cl.
| | | |
|---|---|---|
| *C12N 5/00* | (2006.01) | |
| *A61K 9/00* | (2006.01) | |
| *A61K 35/13* | (2015.01) | |
| *A61K 35/545* | (2015.01) | |
| *C12N 5/02* | (2006.01) | |
| *C12N 5/074* | (2010.01) | |
| *A01N 63/00* | (2020.01) | |
| *A61P 15/02* | (2006.01) | |
| *A61P 25/28* | (2006.01) | |
| *A61P 35/00* | (2006.01) | |

(52) U.S. Cl.
CPC .......... *A61K 35/545* (2013.01); *A61K 9/0019* (2013.01); *A61K 35/13* (2013.01); *C12N 5/0607* (2013.01); *A61P 15/02* (2018.01); *A61P 25/28* (2018.01); *A61P 35/00* (2018.01)

(58) Field of Classification Search
CPC ........ C12N 5/0607; A61K 35/15; A61P 35/00
See application file for complete search history.

(56) References Cited

U.S. PATENT DOCUMENTS

| | | | |
|---|---|---|---|
| 9,029,146 B2 * | 5/2015 | Lim et al. | |
| 9,034,335 B2 | 5/2015 | Herrera Sanchez et al. | |
| 2010/0323027 A1 | 12/2010 | Lim et al. | |

OTHER PUBLICATIONS

Reagan et al. Multiple myeloma mesenchymal stem cells: Characterization, origin, and tumor-promoting effects. Clin. Cancer Res. 18:342-349, (Year: 2012).*
Pawitan, J.A. Prospect of stem cell conditioned medium in regenerative medicine. BioMed. Research International, vol. 2014, Article ID 965849, pp. 1-14, (Year: 2014).*
Hulsart-Billstrom et al. A surprisingly poor correlation between in vitro and in vivo testing of biomaterials for bone regeneration. European Cells and Materials 31:312-322, (Year: 2016).*
Kitsis et al. Discordance between gene regulation in vitro and in vivo. Gene Expression 2:313-318, (Year: 1992).*

* cited by examiner

*Primary Examiner* — Quang Nguyen
(74) *Attorney, Agent, or Firm* — Bajwa IP Law Firm; Haris Zaheer Bajwa

(57) ABSTRACT

A method for modifying gene expression of diseased cells in a patient including preparing an extract of diseased cells, forming a plurality of conditioned stem cells by treating a plurality of normal stem cells with a solution of the extract of the diseased cells with a volume ratio between $10^{-15}$ volume/volume (v/v) and $10^{-3}$ v/v (volume of the extract of the diseased cells/volume of a culture medium), forming a conditioned stem cell-derived extract, and forming a plurality of healthy cells by treating the diseased cells with the conditioned stem cell-derived extract.

8 Claims, 4 Drawing Sheets

CONDITIONED STEM CELL-DERIVED EXTRACT

CROSS-REFERENCE TO RELATED APPLICATION

This application claims the benefit of priority from U.S. Provisional Patent Application Ser. No. 62/619,168, filed on Jan. 19, 2018, and entitled "PERSONALIZED AND PRECISE WHOLE EPIGENOME MODIFICATION," which is incorporated herein by reference in its entirety.

TECHNICAL FIELD

The present disclosure generally relates to the field of epigenetic therapy and transcriptome therapy, particularly to a method for modifying gene expression of diseased cells, and more particularly to a method for modifying gene expression of diseased cells using a conditioned stem cell-derived extract.

BACKGROUND

Epigenetic deregulation plays a pivotal role in animal and human diseases and may be rarely restricted to one DNA position, a single miRNA, or histone amino acids. For example, it has been shown that mesenchymal stem cells in multiple myeloma and endometriosis have deregulations in their epigenomes which contribute to the pathology of mesenchymal stem cells in this disease. Therefore, modifying gene expression in diseased cells may be considered as a possible treatment for reversing the diseased cells to an epigenetically normal state and rectifying the disease.

However, conventional genetic and epigenetic therapies have several shortcomings such as being too general that modify epigenetic patterns independent to the personalized epigenetic deregulations in each patient or being too specific and limited to a DNA site or other epigenetic modifications. Therefore, there is a need for a personalized epigenetic treatment that may modify more than one epigenetic deregulations depending on the personalized epigenetic pathology in each patient.

SUMMARY

This summary is intended to provide an overview of the subject matter of the exemplary embodiments of the present disclosure, and is not intended to identify essential elements or key elements of the subject matter, nor is it intended to be used to determine the scope of the claimed implementations. The proper scope of the exemplary embodiments of the present disclosure may be ascertained from the claims set forth below in view of the detailed description below and the drawings.

In one general aspect, the present disclosure describes an exemplary method for modifying gene expression of diseased cells in a patient including preparing an extract of diseased cells, forming a plurality of conditioned stem cells by treating a plurality of normal stem cells with the extract of diseased cells, forming a conditioned stem cell-derived extract, and forming a plurality of healthy cells by treating the diseased cells with the conditioned stem cell-derived extract.

The above general aspect may include one or more of the following features. In some exemplary embodiments, preparing the extract of diseased cells may include isolating diseased cells from a patient, and forming the extract of diseased cells by mixing an alcoholic solution with the diseased cells. In some exemplary embodiments, the alcoholic solution may include at least one of glycerol, ethanol, and combinations thereof. In one or more exemplary embodiments, the alcoholic solution may include glycerol and ethanol with a volume ratio between about 70:30 and about 30:70 (glycerol:ethanol).

According to some exemplary embodiments, forming the extract of diseased cells by mixing the alcoholic solution with the diseased cells may include mixing the alcoholic solution with the diseased cells for a period of time of at least about 7 days to obtain a homogenous extract of diseased cells. In some exemplary embodiments, forming a plurality of conditioned stem cells by treating the plurality of normal stem cells with the extract of diseased cells may include treating the plurality of normal stem cells with a solution of the extract of diseased cells with a volume ratio between about $10^{-15}$ and about $10^{-3}$. volume/volume (v/v) and about $10^{-3}$ v/v (volume of the extract of the diseased cells/volume of the culture medium)

According to some exemplary embodiments, forming conditioned stem cell-derived extract may include culturing the conditioned stem cells in a culture medium, and forming the conditioned stem cell-derived extract by mixing an alcoholic solution with the conditioned stem cells with a concentration between about $10^4$ cell/ml and about $5\times10^4$ cell/ml. In some exemplary embodiments, forming the conditioned stem cell-derived extract by mixing the alcoholic solution with the conditioned stem cells may include mixing the alcoholic solution with the conditioned stem cells for a period of time between about 1 day and about 7 days to obtain a homogenous conditioned stem cell-derived extract.

According to some exemplary embodiments, culturing the conditioned stem cells in the culture medium may include culturing the conditioned stem cells in the culture medium for a time period between about 3 days and about 10 days. In some exemplary embodiments, culturing the conditioned stem cells in the culture medium may include culturing the conditioned stem cells in the culture medium with confluency between about 30% and about 80%.

According to some exemplary embodiments, the conditioned stem cell-derived extract may include the cell-free conditioned stem cell-derived extract. In some exemplary embodiments, the conditioned stem cell-derived extract may include a plurality of secreted proteins from the conditioned stem cells.

According to some exemplary embodiments, forming the plurality of healthy cells by treating the diseased cells with the conditioned stem cell-derived extract may include treating the diseased cells with a solution of the conditioned stem cell-derived extract with a volume ratio between about $10^{-15}$ volume/volume (v/v) and about $10^{-3}$ v/v (volume of the conditioned stem cell-derived extract/volume of the culture medium). In some exemplary embodiments, modifying gene expression of diseased cells may include at least one of epigenetic modification of nucleus, epigenetic modification of mitochondria, or combinations thereof.

According to some exemplary implementations, the method may further include administering the plurality of healthy cells to the patient. In some exemplary embodiments, administering the plurality of healthy cells to the patient may include at least one of local administration, systemic administration, or combinations thereof. In some exemplary embodiments, administering the plurality of healthy cells to the patient may include autologous administration.

BRIEF DESCRIPTION OF THE DRAWINGS

The drawing figures depict one or more implementations in accordance with the present teachings, by way of example only, not by way of limitation. In the figures, like reference numerals refer to the same or similar elements.

DETAILED DESCRIPTION

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Stem cells provide a microenvironment with a wide range of secreted factors, such as growth factors, cytokines, and chemokines. The secreted factors may be referred to as secretome and may be found in the medium where the stem cells are cultured. Secretome of stem cells under specific conditions may be called conditioned stem cell-derived extract which may be used for modifying gene expression of other cells.

In the present disclosure, an exemplary conditioned stem cell-derived extract may be produced by conditioning stem cells using an extract of diseased cells of a patient. The present exemplary conditioned stem cell-derived extract may induce personalized epigenetic modifications in the diseased cells of each respective patient by precisely modifying and correcting their epigenetic deregulations and gene expression.

Disclosed herein is an exemplary method for modifying gene expression of the diseased cells of a patient with at least one of cancer, multiple sclerosis (MS), autism, endometriosis, or any diseases caused or accompanied by epigenetic abnormalities using a personalized conditioned stem cell-derived extract for modifying the epigenome of the diseased cells towards the normal state. The diseased cells may include diseased cells of at least one of cancer, multiple sclerosis (MS), autism, endometriosis, or any diseases caused or accompanied by epigenetic abnormalities.

Figure 1:
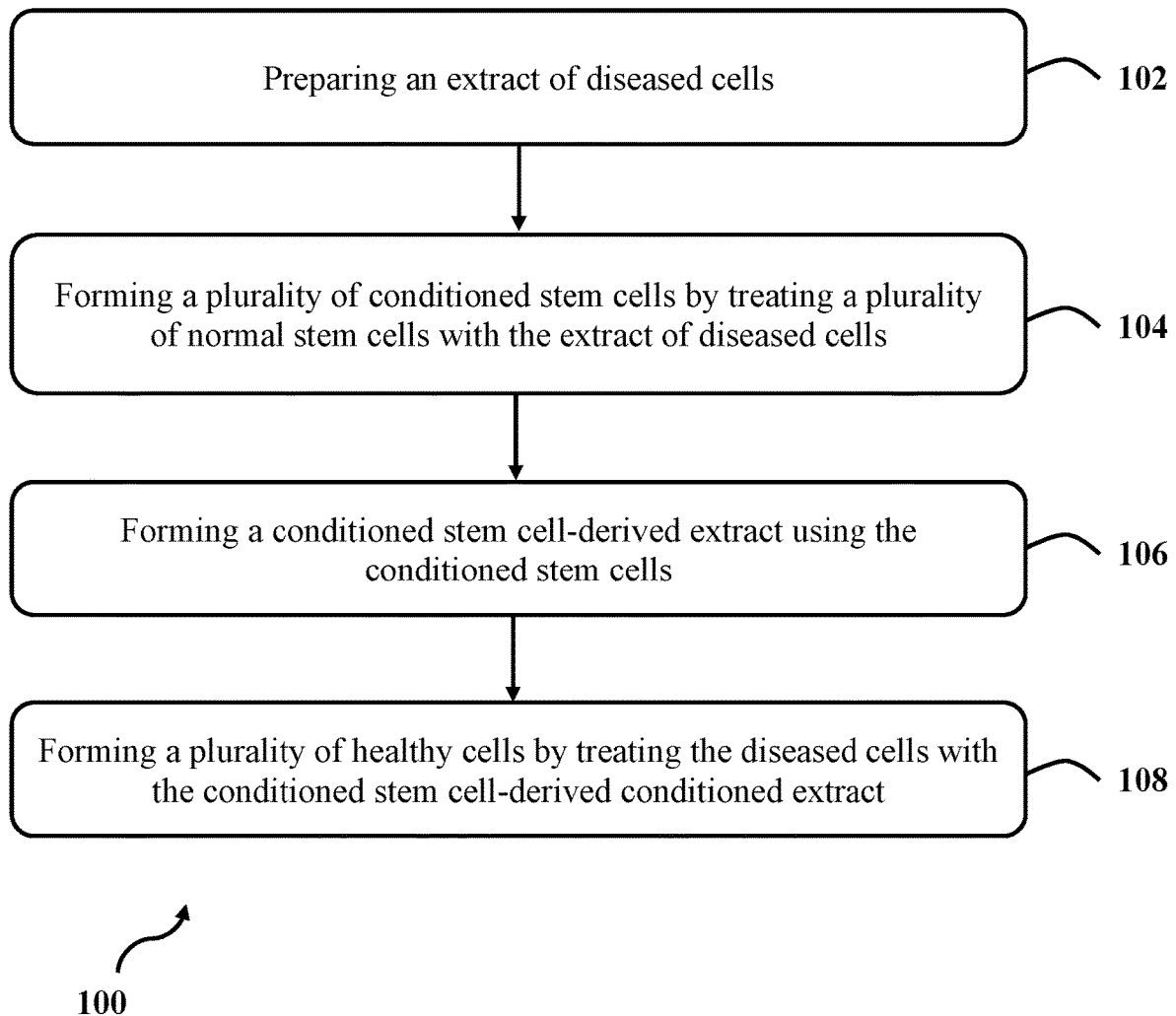
FIG. 1 illustrates a method for modifying gene expression of diseased cells of a patient, consistent with one or more exemplary of the present disclosure.

FIG. 1 shows method 100 for modifying gene expression of diseased cells of a patient, consistent with one or more exemplary embodiments of the present disclosure. Method 100 may include preparing an extract of diseased cells (102), forming a plurality of conditioned stem cells by treating a plurality of normal stem cells with the extract of diseased cells (104), forming a conditioned stem cell-derived extract using the conditioned stem cells (106), and forming a plurality of healthy cells by treating the diseased cells with the conditioned stem cell-derived extract (108).

Step 102 may include preparing the extract of diseased cells. In some exemplary implementations, preparing the extract of diseased cells may include isolating diseased cells from a patient, and forming the extract of diseased cells by mixing an alcoholic solution with the diseased cells. In one or more exemplary implementations, preparing the extract of diseased cells may further include culturing the diseased cells.

In some exemplary embodiments, isolating the diseased cells may include isolating the diseased cells from primary tumors, metastatic tumors, or pathologic tissues. In some exemplary embodiments, isolating the diseased cells may include isolating the diseased cells using bone marrow aspiration. In some exemplary embodiments, isolating diseased cells from a patient may include isolating diseased cells from a patient with at least one of cancer, multiple sclerosis (MS), autism, endometriosis, multiple myeloma, and any diseases caused or accompanied by epigenetic abnormalities. In some exemplary embodiments, the diseased cells may be diseased stem cells such as diseased mesenchymal stem cells.

In some exemplary embodiments, culturing the diseased cells may include culturing the diseased cells using at least one of Dulbecco's modified Eagle medium nutrient mixture F-12 (DMEM/F-12), Roswell Park Memorial Institute medium (RPMI-1640), minimum essential medium (MEM), alpha medium (a-MEM), medium 199, and Iscove's modified Dulbecco's medium (IMDM), and combinations thereof. In some exemplary embodiments, culturing the diseased cells may include culturing the diseased cells in a culture medium to obtain a cellular confluency between about 30% and about 100%. In some exemplary embodiments, the diseased cells may be cultured and used for producing conditioned stem cell-derived extract. In an exemplary embodiment, the diseased cells may be used directly for producing conditioned stem cell-derived extract without any culturing.

In some exemplary implementations, mixing the alcoholic solution with the diseased cells may include mixing the alcoholic solution with the diseased cells with a concentration between $10^4$ cell/ml and about $5 \times 10^4$ cell/ml. In some exemplary embodiments, forming the extract of diseased cells by mixing the alcoholic solution with the diseased cells may include mixing the alcoholic solution with the diseased cells for a period of time of at least about 7 days to obtain a homogenous extract of diseased cells.

In some exemplary implementations, mixing the alcoholic solution with the diseased cells may include at least one of pipetting, stirring, vortexing, or combinations thereof. In some exemplary embodiments, the alcoholic solution may include at least one of glycerol, ethanol, and combinations thereof. In one or more exemplary embodiments, the alcoholic solution may include glycerol and ethanol with a volume ratio of glycerol and ethanol between about 70:30 and about 30:70 (glycerol:ethanol). In some exemplary embodiments, the alcoholic solution may be diluted in distilled water (DW). In some exemplary embodiments, the extract of diseased cells may be stored at a temperature of about 4° C. or at room temperature for a time period of at least about 1 day.

Step 104 may include forming the plurality of conditioned stem cells by treating the plurality of normal stem cells with the extract of diseased cells. In some exemplary embodiments, the plurality of normal stem cells may include at least one of bone marrow mesenchymal stem cells, adipose tissue mesenchymal stem cells, endometrial mesenchymal stem cells, or combinations thereof. In some exemplary embodiments, forming a plurality of conditioned stem cells by treating the plurality of normal stem cells with the extract of diseased cells may include treating the plurality of normal stem cells with a solution of the extract of the diseased cells with a volume ratio between about $10^{-15}$ volume/volume (v/v) and about $10^{-3}$ v/v (volume of the extract of the diseased cells/volume of the culture medium).

In some exemplary embodiments, treating the plurality of normal stem cells with the extract of diseased cells may be repeated once or twice a day for a time period between 1 day and 7 days. In some exemplary embodiments, a diluted extract of diseased cells may be prepared by diluting the extract of diseased cells for about $10^3$ to about $10^{15}$ times of concentration of the extract of diseased cells in distilled water or in a culture medium. In some exemplary embodiments, the extract of diseased cells may be diluted by a serial dilution in a scale of $\frac{1}{10}$ using distilled water.

In one or more exemplary embodiments, after each step of dilution, the diluted extract of diseased cells may be homogenized by stirring for a period of time of about more than 15 seconds. In some exemplary embodiments, forming a plurality of conditioned stem cells by treating the plurality of normal stem cells with the extract of diseased cells may include treating the plurality of normal stem cells with the diluted extract of diseased cells with a volume ratio between about $10^{-15}$ volume/volume (v/v) and about $10^{-3}$ v/v (volume of the extract of the diseased cells/volume of the culture medium).

In some exemplary embodiments, the last dilution may be done in culture medium instead of distilled water. In one or more exemplary embodiments, the culture medium may include at least one of Dulbecco's modified Eagle medium nutrient mixture F-12 (DMEM/F-12), Roswell Park Memorial Institute medium (RPMI-1640), minimum essential medium (MEM), Alpha medium (a-MEM), medium 199, and Iscove's modified Dulbecco's medium (IMDM), and combinations thereof. In some exemplary embodiments, the plurality of conditioned stem cells may be stored at room temperature or at a temperature of about 4° C. for at least 1 day.

Step 106 may include forming the conditioned stem cell-derived extract using the conditioned stem cells. In some exemplary implementation, forming the conditioned stem cell-derived extract using the conditioned stem cells may include culturing the conditioned stem cells in a culture medium and forming the conditioned stem cell-derived extract by mixing the alcoholic solution with the conditioned stem cells.

In some exemplary embodiments, culturing the conditioned stem cells in the culture medium may include culturing the conditioned stem cells in the culture medium for a time period between about 3 days and about 10 days. In some exemplary embodiments, culturing the conditioned stem cells in the culture medium may include culturing the conditioned stem cells in the culture medium with confluency between about 30% and about 80%.

In some exemplary embodiments, the alcoholic solution may include at least one of glycerol, ethanol, and combinations thereof. In some exemplary embodiments, the alcoholic solution may include glycerol and ethanol with a volume ratio between about 70:30 and about 30:70 (glycerol:ethanol). In some exemplary embodiments, forming the conditioned stem cell-derived extract by mixing the alcoholic solution with the conditioned stem cells may include mixing the alcoholic solution with the diseased cells for a period of time between about 1 day and about 7 days to obtain a homogenous conditioned stem cell-derived extract.

In some exemplary embodiments, forming the conditioned stem cell-derived extract may include forming the cell-free conditioned stem cell-derived extract. In some exemplary embodiments, forming the cell-free conditioned stem cell-derived extract may include removing the conditioned stem cells from the conditioned stem cell-derived extract using at least one of centrifugation, filtration, and combinations thereof.

In some exemplary embodiments, the conditioned stem cell-derived extract may include a plurality of secreted proteins from the conditioned stem cells. In some exemplary embodiments, the conditioned stem cell-derived extract may be stored at room temperature or at a temperature of about 4° C. In some exemplary embodiments, the conditioned stem cell-derived extract may be used to modify epigenetic or gene expression characteristics of disease cells toward normal epigenetic or genes expression state.

Step 108 may include forming the plurality of healthy cells by treating the diseased cells with the conditioned stem cell-derived extract. In some exemplary embodiments, forming the plurality of healthy cells by treating the diseased cells with the conditioned stem cell-derived extract may include treating the diseased cells with a solution of the conditioned stem cell-derived extract with a volume ratio between about 10' volume/volume (v/v) and about $10^{-3}$ v/v (volume of the conditioned stem cell-derived extract/volume of the culture medium).

In some exemplary embodiments, treating the diseased cells with the conditioned stem cell-derived extract may lead to modification of gene expression in diseased cells. In some exemplary embodiments, modification of gene expression in diseased cells may include at least one of epigenetic modification of nucleus, modification of mitochondria, modification of a number of mitochondria, or combinations thereof. In some exemplary implementations, modification of gene expression in diseased cells may include modification of reactive oxygen species (ROS) levels.

In some exemplary implementations, the exemplary method may further include administering the plurality of healthy cells to the patient. In some exemplary embodiments, administering the plurality of healthy cells to the patient may include at least one of local administration, systemic administration, or combinations thereof. In some exemplary embodiments, administering the plurality of healthy cells to the patient may include autologous administration.

EXAMPLES

Example 1: Modifying Gene Expression of Diseased Cells Using a Conditioned Stem Cell-Derived Extract In this example, gene expression of endometriotic or multiple myeloma diseased cells of a patient was modified and a plurality of healthy cells were formed using an exemplary conditioned stem cell-derived extract through the steps of preparing an extract of diseased cells, forming a plurality of conditioned stem cells by treating a plurality of normal stem cells with the extract of diseased cells, forming a conditioned stem cell-derived extract using the conditioned stem cells, and forming a plurality of healthy cells by treating the diseased cells with the conditioned stem cell-derived extract.

At first, endometriotic and multiple myeloma diseased cells were isolated from a patient, and cultured in DMEM/F-12 medium to obtain a cellular confluency between about 30% and about 100%. Afterward, the extract of diseased cells was formed by mixing the alcoholic solution with the diseased cells with a concentration of about $10^{-5}$ ml/cell for 7 days using a vortex mixer to obtain a homogenous extract of diseased cells. The alcoholic solution included glycerol and ethanol with a volume ratio of about 70:30 (glycerol:ethanol). After that, the extract of diseased cells was stored at a temperature of about 4° C. for about 1 day.

In the next step, the plurality of conditioned stem cells was formed by treating the plurality of normal bone marrow stem cells with the extract of diseased cells. At first, normal bone marrow stem cells were isolated from normal persons without apparent known genetic or systematic disorders and cultured in DMEM medium. Stemness of normal bone marrow stem cells of passage 2 was characterized either by studying their surface antigens, cluster of differentiation (CD) markers, such as CD44, CD73, CD90, CD105 or differentiation potential by in-vitro osteogenic and adipogenic differentiation of mesenchymal stem cells.

After that, the plurality of conditioned stem cells was formed by treating the plurality of normal stem cells with a diluted extract of diseased cells with a volume ratio of about 10' v/v (volume of the extract of the diseased cells/volume of the culture medium). twice a day for about 3 days. The diluted extract of diseased cells had a concentration of about 0.001% of the extract of diseased cells. The extract of diseased cells was diluted by a serial dilution in a scale of $\frac{1}{10}$ using distilled water and after each step of dilution, the diluted extract of diseased cells was homogenized by stirring for a period of time of about 15 seconds. The last dilution was done in culture medium instead of distilled water. Afterward, the plurality of conditioned stem cells was stored at room temperature or at a temperature of about 4° C. for 7 days.

In the next step, the conditioned stem cell-derived extract was formed using the conditioned stem cells by culturing the conditioned stem cells in a culture medium and forming the conditioned stem cell-derived extract by mixing the alcoholic solution with the conditioned stem cells. The conditioned stem cells were cultured in the culture medium for about 7 days until the confluency of the conditioned stem cells reached about 40%

Mixing the alcoholic solution with the conditioned stem cells was done using a vortex mixer for a time period of about 15 seconds to obtain a homogenous conditioned stem cell-derived extract. The alcoholic solution included glycerol and ethanol with a volume ratio of about 70:30 (glycerol:ethanol). The cell-free conditioned stem cell-derived extract was stored at room temperature or at a temperature of about 4° C.

In the last step, the prepared cell-free conditioned stem cell-derived extract was used to modify epigenetic or gene expression characteristics of disease cells toward normal epigenetic or genes expression state. The plurality of healthy cells was formed by incubating the diseased cells with a solution of the cell-free conditioned stem cell-derived extract with a volume ratio of about $10^{-6}$ v/v (volume of the cell-free conditioned stem cell-derived extract/volume of the culture medium). for a time period of about 7 days.

Treating the diseased cells with the conditioned stem cell-derived extract led to modification of gene expression in diseased cells, for example, epigenetic modification of nucleus, epigenetic modification of mitochondria, or combinations thereof. The conditioned stem cell-derived extract was personalized and had precise epigenetic effects, in addition to gene expression effects on the diseased cells.

Example 2: Characterization of Modified Multiple Myeloma Diseased Cells

In this example, the modified multiple myeloma diseased cells were characterized after treating with the conditioned stem cell-derived extract. Alkaline phosphatase (ALP) is a marker of osteogenic differentiation and have an abnormal expression in diseased mesenchymal stem cells. Therefore, this experiment was conducted by measuring alkaline phosphatase expressions of normal stem cells and multiple myeloma diseased cells before and after treatment using real-time polymerase chain reaction (PCR).

Figure 2:
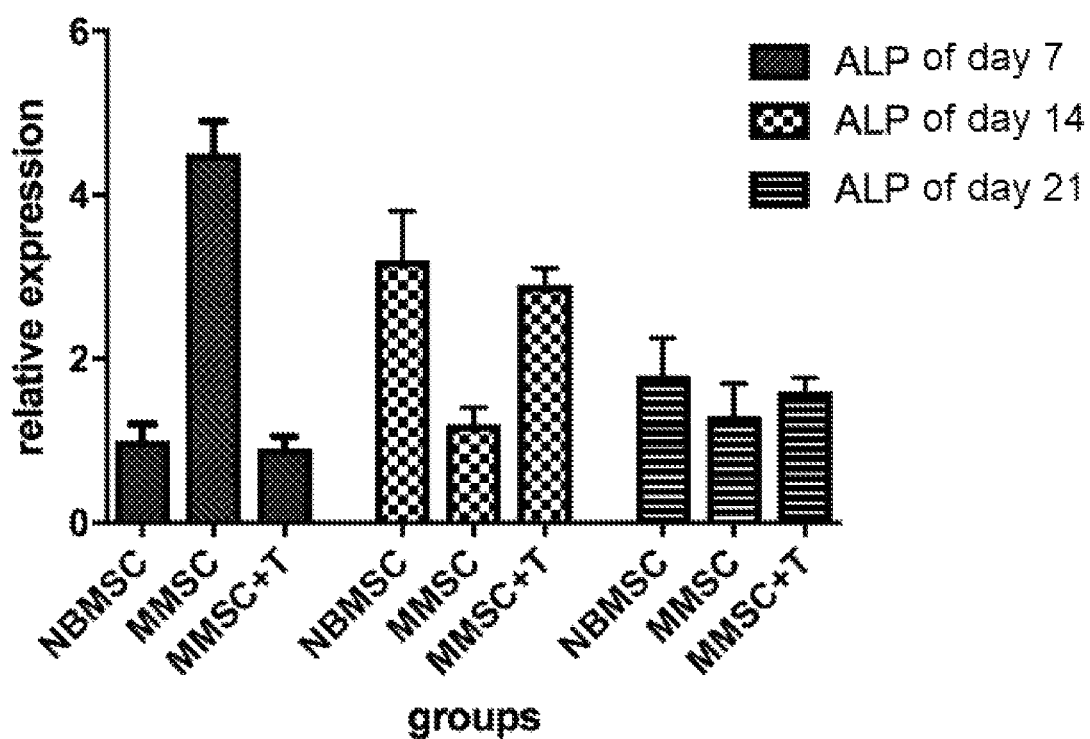
FIG. 2 illustrates a relative expression of alkaline phosphatase in multiple myeloma diseased cells before and after treatment with the conditioned stem cell-derived extract at different days, consistent with one or more exemplary embodiments of the present disclosure.

FIG. 2 shows the relative expression of alkaline phosphatase in normal bone marrow mesenchymal stem cells (NBMSC), multiple myeloma mesenchymal stem cells (MMSC), and multiple myeloma mesenchymal stem cells after treatment with the conditioned stem cell-derived extract (MMSC+T at days 7, 14, and 21), consistent with one or more exemplary embodiments of the present disclosure.

Referring to FIG. 2, comparing the ALP expression through osteogenic differentiation of multiple myeloma mesenchymal stem cells (MMSC) before and after treatment with the conditioned stem cell-derived extract and the normal bone marrow mesenchymal stem cells (NBMSC) indicates the effect of the conditioned stem cell-derived extract on normalization of ALP expression pattern through osteogenic differentiation in multiple myeloma mesenchymal stem cells (MMSC). The abnormal expression of ALP at days 7, 14, and 21 in the MMSC significantly changed and became normal due to the treatment of the MMSC with the conditioned stem cell-derived extract.

Furthermore, different histone deacetylases (HDACs), interleukin 6 (IL-6), and vascular endothelial growth factor (VEGF) have abnormal expressions in multiple myeloma and these genes have pathogenic functions and epigenetic functions in multiple myeloma stem cells. Therefore, expressions of different histone deacetylases (HDACs), interleukin 6 (IL-6), and vascular endothelial growth factor (VEGF) were measured by specific primers and real-time PCR reaction before and after treatment.

Figure 3:
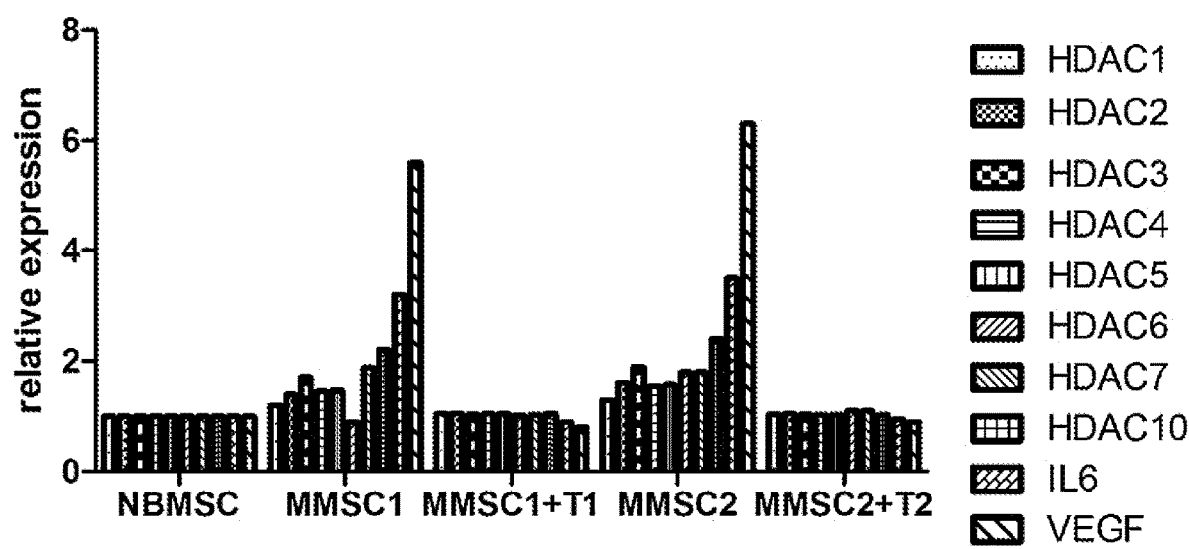
FIG. 3 illustrates a relative expression of different histone deacetylases (HDACs), interleukin 6 (IL-6), and vascular endothelial growth factor (VEGF), consistent with one or more exemplary embodiments of the present disclosure.

FIG. 3 shows relative expression of different HDACs, IL-6, and VEGF in normal bone marrow mesenchymal stem cells (NBMSC), multiple myeloma mesenchymal stem cells from a patient 1 (MMSC1), multiple myeloma mesenchymal stem cells from a patient 2 (MMSC2), multiple myeloma mesenchymal stem cells of patient 1 after treatment with the conditioned stem cell-derived extract (MMSC1+T1), and multiple myeloma mesenchymal stem cells of patient 2 after treatment with the conditioned stem cell-derived extract (MMSC2+T2), consistent with one or more exemplary embodiments of the present disclosure.

Referring to FIG. 3, comparison between the expressions of HDACs, IL-6, and VEGF in the multiple myeloma mesenchymal stem cells (MMSC1 and MMSC2) groups before and after treatment with the conditioned stem cell-derived extract of the present disclosure and the and NBMSC group revealed the effect of the conditioned stem cell-derived extract on normalization of HDACs, IL-6, and VEGF expression patterns in multiple myeloma mesenchymal stem cells (MMSC). The abnormal expression of HDACs, IL-6, and VEGF in the MMSC significantly changed and became normal due to the personalized treatment of the MMSC with the conditioned stem cell-derived extract.

Example 3: Characterization of Modified Endometriosis Diseased Cells

In this example, the modified endometriotic diseased cells were characterized after treating with the conditioned stem cell-derived extract. This experiment was conducted by measuring expressions of DNA methyltransferase 1 (DNMT1), beta-catenin (β-catenin), and vascular endothelial growth factor (VEGF) in normal stem cells and endometriotic diseased cells before and after treatment using real-time polymerase chain reaction (PCR). DNMT1 is one of the main genes involved in epigenetic regulations and is proved to be deregulated in endometrial disease. Also, β-catenin and VEGF are proved to be deregulated in endometrial disease.

Figure 4:
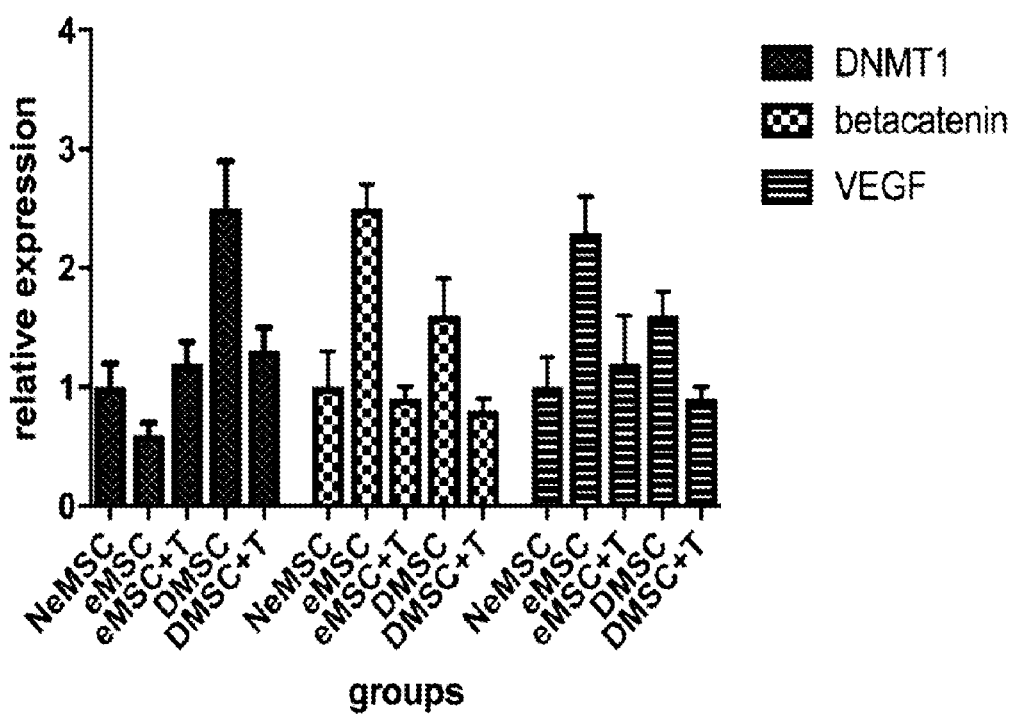
FIG. 4 illustrates a relative expression of DNA methyltransferase 1 (DNMT1), beta-catenin (β-catenin), and vascular endothelial growth factor (VEGF) in endometriotic diseased cells before and after treatment with the conditioned stem cell-derived extract, consistent with one or more exemplary embodiments of the present disclosure.

FIG. 4 shows the relative expression of DNMT1, β-catenin, and VEGF in normal endometrial mesenchymal stem cells (NeMSC), endometriotic endometrial mesenchymal stem cells (eMSC), endometrial stem cells from a patient with endometrial disease other than endometriosis (DMSC), endometriotic endometrial mesenchymal stem cells after treatment with the conditioned stem cell-derived extract (eMSC+T), and endometrial stem cells from a patient with endometrial disease other than endometriosis after treatment with the conditioned stem cell-derived extract (DMSC+T), consistent with one or more exemplary embodiments of the present disclosure.

Referring to FIG. 4, a comparison between the DNMT1, β-catenin, and VEGF expressions of the test groups before and after treatment indicates the effect of the conditioned stem cell-derived extract on normalizing the expressions of DNMT1, β-catenin, and VEGF in the eMSC and DMSC groups. The abnormal expression of DNMT1 in the eMSC and DMSC groups significantly changed and became normal due to the treatment of the eMSC and DMSC with the conditioned stem cell-derived extract. Also, the abnormal expression of β-catenin and VEGF in the eMSC and DMSC groups significantly decreased and became normal due to the treatment of the eMSC and DMSC with the conditioned stem cell-derived extract.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A method for in vitro modification of gene expression of human multiple myeloma mesenchymal stem cells with epigenetic deregulation, comprising:
   preparing an extract of the human multiple myeloma mesenchymal stem cells of a patient, comprising:
      isolating the human multiple myeloma mesenchymal stem cells from the patient; and
      forming the extract of human multiple myeloma mesenchymal stem cells by mixing an alcoholic solution with the human multiple myeloma mesenchymal stem cells, the alcoholic solution comprising glycerol and ethanol with a volume ratio of 70:30, respectively;
   forming a plurality of conditioned normal human bone marrow mesenchymal stem cells in a culture medium by treating a plurality of normal human bone marrow mesenchymal stem cells with a solution of the extract of the human multiple myeloma mesenchymal stem cells with a volume ratio between $10^{-15}$ volume/volume (v/v) and $10^{-3}$ v/v (volume of the extract of the human multiple myeloma mesenchymal stem cells/volume of the culture medium);
   forming a conditioned normal human bone marrow mesenchymal stem cell-derived extract based on the plurality of conditioned normal human bone marrow mesenchymal stem cells, comprising:
      culturing the conditioned normal human bone marrow mesenchymal stem cells in a culture medium; and
      forming the conditioned normal human bone marrow mesenchymal stem cell-derived extract by mixing an alcoholic solution with the conditioned normal human bone marrow mesenchymal stem cells, the alcoholic solution comprising glycerol and ethanol with a volume ratio of 70:30, respectively; and
   forming a plurality of human multiple myeloma mesenchymal stem cells with normal gene expression by treating the human multiple myeloma mesenchymal stem cells in a culture medium with the conditioned normal human bone marrow mesenchymal stem cell-derived extract.

2. The method according to claim 1, wherein forming the extract of human multiple myeloma mesenchymal stem cells by mixing the alcoholic solution with the human multiple myeloma mesenchymal stem cells comprises mixing the alcoholic solution with the human multiple myeloma mesenchymal stem cells for a period of time of at least 7 days until a homogenous extract of human multiple myeloma mesenchymal stem cells is obtained.

3. The method according to claim 1, wherein forming the conditioned normal human bone marrow mesenchymal stem cell-derived extract comprises mixing the alcoholic solution with the conditioned normal human bone marrow mesenchymal stem cells for a period of time between 1 day and 7 days.

4. The method according to claim 1, wherein culturing the conditioned normal human bone marrow mesenchymal stem cells in the culture medium comprises culturing the conditioned normal human bone marrow mesenchymal stem cells in the culture medium for a time period between 3 days and 10 days.

5. The method according to claim 1, wherein culturing the conditioned normal human bone marrow mesenchymal stem cells in the culture medium comprises culturing the conditioned normal human bone marrow mesenchymal stem cells in the culture medium with confluency between 30% and 80%.

6. The method according to claim 1, wherein forming the plurality of human multiple myeloma mesenchymal stem cells with normal gene expression by treating the human multiple myeloma mesenchymal stem cells in a culture medium with the conditioned normal human bone marrow mesenchymal stem cell-derived extract with a volume ratio between $10^{-15}$ volume/volume (v/v) and about $10^{-3}$ v/v (volume of the extract of the conditioned normal human bone marrow mesenchymal stem cells/volume of the culture medium).

7. The method according to claim 1, wherein the conditioned normal human bone marrow mesenchymal stem cell-derived extract comprises a cell-free conditioned normal human bone marrow mesenchymal stem cell-derived extract.

8. The method according to claim 1, wherein the conditioned normal human bone marrow mesenchymal stem cell-derived extract comprises a plurality of secreted proteins from the conditioned normal human bone marrow mesenchymal stem cells.

* * * * *